US012691202B1

(12) United States Patent　(10) Patent No.:　US 12,691,202 B1
Albanna　(45) Date of Patent:　Jul. 28, 2026

(54) ACELLULAR DERMAL MATRIX FOR SKIN AND SURGICAL RECONSTRUCTION AND METHODS OF MAKING SAME

(71) Applicant: Humabiologics, Inc., Phoenix, AZ (US)

(72) Inventor: Mohammad Z. Albanna, Chandler, AZ (US)

(73) Assignee: HUMABIOLOGICS, INC, Phoenix, AZ (US)

(*) Notice: Subject to any disclaimer, the term of this patent is extended or adjusted under 35 U.S.C. 154(b) by 0 days.

(21) Appl. No.: 19/305,754

(22) Filed: Aug. 20, 2025

(51) Int. Cl.
| | |
|---|---|
| *A61L 27/24* | (2006.01) |
| *A61L 27/36* | (2006.01) |
| *A61L 27/54* | (2006.01) |
| *C12N 9/16* | (2006.01) |
| *C12N 9/76* | (2006.01) |

(52) U.S. Cl.
CPC ............. *A61L 27/24* (2013.01); *A61L 27/362* (2013.01); *A61L 27/3687* (2013.01); *A61L 27/54* (2013.01); *C12N 9/16* (2013.01); *C12N 9/6427* (2013.01); *A61L 2300/414* (2013.01); *A61L 2300/64* (2013.01); *A61L 2430/34* (2013.01); *C12Y 301/30002* (2013.01); *C12Y 304/21004* (2013.01)

(58) Field of Classification Search
None
See application file for complete search history.

(56) References Cited

U.S. PATENT DOCUMENTS

| | | | |
|---|---|---|---|
| 8,067,149 | B2 | 11/2011 | Livesey et al. |
| 9,623,149 | B2 | 4/2017 | Chun et al. |
| 2012/0189707 | A1 | 7/2012 | Chun et al. |
| 2014/0072629 | A1 | 3/2014 | DePaula et al. |
| 2020/0229915 | A1 | 7/2020 | Ye et al. |
| 2021/0393396 | A1 | 12/2021 | Kim et al. |
| 2024/0390553 | A1 | 11/2024 | Xu et al. |
| 2025/0049988 | A1 | 2/2025 | Castillo et al. |
| 2025/0222171 | A1 | 7/2025 | Woo et al. |

FOREIGN PATENT DOCUMENTS

CN　102218162 A　*　10/2011

OTHER PUBLICATIONS

Wenta et al. (Remodeling of the extracellular matrix by serine proteases as a prerequisite for cancer initiation and progression, Matrix Biology 134 (2024) 197-219) (Year: 2024).*
Matuska et al. (The effect of terminal sterilization on structural and biophysical properties of a decellularized collagen based scaffold; implications for stem cell adhesion, Society for Biomaterials, published online Jun. 3, 2014) (Year: 2014).*
Visikol (The importance of Dehydration and Rehydration of fixed tissue for Immunolabeling, available online Aug. 10, 2022) (Year: 2022).*
Zammit et al. (Meshed acellular dermal matrix: technique and application in implant based breast reconstruction, Plast Aesthet Res 2016; 3:254-6). (Year: 2016).*
Dehydration Protocol (Creative Bioarray, available online Apr. 17, 2025).*

* cited by examiner

*Primary Examiner* — Melissa S Mercier
(74) *Attorney, Agent, or Firm* — Invention To Patent Services; Alex Hobson

(57) ABSTRACT

An acellular dermal matrix (ADM) is produced using a series of steps that maintains a high percentage of collagen, hydrates quickly and maintains high mechanical properties. The ADM is aseptically processed and requires no terminal sterilization. The basement membrane may be preserved in the ADM. The ADM may hydrate very quickly, wherein the ADM doubles in weight within 10 seconds or less of soaking in water at standard temperature and pressure and may triple in weight within 30 minutes. Also, the ADM may have limited thickness swelling. The ADM may preserve mechanical properties and may have mechanical properties comparable to human skin. The ADM may be decellularized and have very minimal DNA content and be non-immunogenic. The ADM may be manufactured in various sizes and thickness. The ADM may be manufactured without lyophilization or freeze-drying.

9 Claims, 23 Drawing Sheets

10

40

| Test Article | Ultimate Tensile Strength UTS (Mpa) | Failure Strain (%) | Elastic Modulus (Mpa) |
|---|---|---|---|
| ADM Dry | 19.5 | 62 | 52 |
| ADM Wet | 17 | 130 | 30 |
| Human Skin-Back | 13.2 - 30 | 37 - 71 | 48.8 - 118.2 |
| Human Skin-Abdomen | 2 - 15.0 | | 18.8 |
| AlloDerm/FlexHD | 7.5 - 7.7 | 39 | 24 |
| DermaMatrix | 16 | | |

FIG. 10

Native Skin          Decell Skin

Complete
removal of cells

>88% preserved
collagen
structure

Weight Change

Thickness providing a mammalian skin tissue

washing the mammalian skin tissue with an ionic solution

washing the epidermis free tissue to a recombinant serine protease enzyme to destroy the cells to produce a processed dermal tissue

removing residual lipids from the processed dermal tissue using an organic solvent or surfactant-based solution containing one or more of chloroform, methanol, hexane, or surfactants to produce a lipid extracted tissue

washing the lipid extracted tissue with an acid solution for at least 45 minutes to achieve microbial inactivation to produce a microbe-free ADM

washing the microbe-free ADM to a dehydration step using a solution containing one or more of ethanol, methanol, acetone, or xylene to produce a manufactured acellular dermal matrix

FIG. 30

ACELLULAR DERMAL MATRIX FOR SKIN AND SURGICAL RECONSTRUCTION AND METHODS OF MAKING SAME

BACKGROUND OF THE INVENTION

Field of the Invention

The invention relates to acellular dermal matrix that has a high preservation of collagen, hydrates quickly and maintains high mechanical properties.

Background

Manufactured acellular dermal matrix material are used for a wide variety of applications, such as patches that can be grafted onto the skin or internally to an organ. The acellular dermal matrix may have the DNA removed and may have a particular set of physical properties, such as swelling rates and dimensional changes as a result of swelling. Also, the acellular dermal matrix materials may have mechanical properties that provide strength and support to underlying tissue. Current acellular dermal matrix patches have high in plane dimensional changes that can compromise the adhesion to underlying tissue to which the acellular dermal matrix is attached to. Also, current acellular dermal matrix materials may take a long time to absorb fluid. In some cases, a surgeon may have to wait for the acellular dermal matrix to absorb fluid before application to a patient and this can delay application and adds cost to surgery.

SUMMARY OF THE INVENTION

The acellular dermal matrix (ADM) of the present invention is produced using a series of steps that maintains a high percentage of collagen, hydrates quickly and maintains high mechanical properties. The ADM can be aseptically processed and requires no terminal sterilization or may require terminal sterilization. The basement membrane may be preserved in the ADM. The ADM may hydrate very quickly, wherein the ADM doubles in weight within 10 seconds or less of soaking in water at standard temperature and pressure and the ADM may triple in weight within 30 minutes. Also, the ADM may have limited thickness swelling, such as no more than about 50% after 30 minutes soaking in water a standard temperature and pressure. The ADM may preserve mechanical properties and may have mechanical properties comparable to human skin. The ADM may be decellularized and have a very minimal DNA content and be non-immunogenic. The ADM may be manufactured in various sizes and thickness to accommodate various applications and uses.

The ADM may be non-immunogenic having at least 90% of DNA material removed. An exemplary ADM may have less than about 300 ng DNA/mg, less than about 250 ng DNA/mg, 200 ng DNA/mg, less than about 150 ng DNA/mg, less than about 100 ng DNA/mg, less than about 75 ng DNA/mg, less than about 50 ng DNA/mg, less than about 25 ng DNA/mg and any range between and including the values provided.

The process of preparing the ADM renders a clean ADM having low levels of solvents such as xylenes, a benzene containing compound. The residual levels are determined through a cell culture fluorescence test with alamarBlue stain.

AlamarBlue is used for as a cell viability and cytotoxicity assay reagent and is a water-soluble dye that measures the metabolic activity of living cells. AlamarBlue contains resazurin, a non-toxic, cell-permeable compound that is blue and non-fluorescent. In metabolically active (viable) cells, resazurin is reduced to resorufin, which is pink and highly fluorescent. By measuring either fluorescence or colorimetric absorbance of the cell health, and cell proliferation can be measured.

An exemplary ADM may retain a substantial percentage of collagen from the native tissue, such as about 55% or more, about 65% or more, about 75% or more, about 80% or more, about 85% or more, about 90% or more and any range between and including the percentages provided.

An acellular dermal matrix may include a medicant, such as an antibiotic, an anti-inflammatory medicant, a coagulant and the like. Also, the ADM may include additional materials to promote wound healing, such as growth factors that may be added to the acellular dermal matrix, cells and the like.

An acellular dermal matrix may include a plurality of apertures that form an aperture pattern. The apertures may include elongated apertures that are interconnected by nodes, an intersection of two or more elongated apertures. An elongated aperture may have a length that is at least three times a width and may be a slit. Apertures may be formed by a mesher, a device that is commonly used in a procedure facility such as an operating room to produce an aperture pattern in tissue. Meshing the acellular dermal matrix may improve the elongation by allowing the ADM to stretch, such as 2:1, 3:1, or even 4:1 in one direction. The apertures may also aid in healing and integration of the ADM into native tissue as a graft. The apertures may allow for perfusion to aid in healing and to prevent infection. Meshing increases the surface area of the ADM for greater coverage, thereby requiring less ADM material.

The process for making the ADM of the present invention includes a plurality of steps that produce a manufactured ADM that is shelf stable, as described herein. The shelf stable means less susceptible for hydrolytic degradation, microbial growth risk, enzymatic activity. The ADM made according to the method described herein may have better thermal stability, may be lighter weight, may not require refrigeration even during shipment. The process or method of making includes, but is not limited to, soaking the ADM in an ionic solution, such as sodium chloride solution, such as a 1M NaCl or more, 1.5M solution or more, or about 2M NaCl solution or more. The temperature of the solution may be elevated over room temperature, such as about 40° C. or more, or from about 40° C. to about 50° C. The time of soaking may depend on the type of tissue, wherein fresh tissue from a donor may be soaked for about 3 hours or more, about 4 hours or more, about six hours or more, about 8 hours, or from about 4 hours to 8 hours. A frozen tissue may be soaked in the sodium chloride solution for about one hour or more, about 2 hours or more, about three hours or more or from about one to three hours.

The epidermis may be removed from the tissue before or after soaking.

Other ionic solutions may include, but are not limited to, Potassium chloride (KCl)-Calcium chloride (CaCl$_2$)), Magnesium sulfate (MgSO$_4$), Sodium sulfate (Na$_2$SO$_4$), Ammonium chloride (NH$_4$Cl), Sodium bicarbonate (NaHCO$_3$), Sodium chloride (NaCl), Magnesium chloride (MgCl$_2$), Sodium bromide (NaBr), Ammonium nitrate (NH$_4$NO$_3$), Barium sulfate (BaSO$_4$), Sodium carbonate (Na$_2$CO$_3$), and Potassium sulfate (K$_2$SO$_4$).

The tissue may then be washed in deionized water for a DI wash time of about 10 minutes or more, about 15 minutes or more, and the DI water may be set to a temperature of about 40° C. or more, about 45° C. or more or from about 40° C. to about 50° C. A preferred washing time may be about 15 minutes, and a preferred temperature may be about 44° C.

After washing the tissue may be soaked in an enzyme solution, such as TrypLE (Thermo Fisher Scientific Inc) a recombinant enzyme, at a temperature of about 30° C. or more, such as from about 30° C. to about 40° C. for a soak time of about 1.5 hr or more, about 2.0 hr or more, about 2.5 hr or more. A preferred enzyme solution contains recombinant enzyme. TrypLE is a serine protease, which is a class of enzymes of high purity that break peptide bonds. TrypLE is a proteolytic enzyme, which means it breaks down proteins into smaller peptides. TrypLE is produced through recombinant DNA technology.

After the enzyme soaking, the tissue may then be water washed with water such as deionized water for about 15 minutes or more at a temperature of about 35° C. or more, or about 40° C. more, such as about 44° C.

After the water washing, the tissue may be soaked in 70% Ethanol at a temperature of about 35° C. or more, or about 40° C. more, such as about 44° C. for a soak time of about 2 hr or more, about 2.5 hr or more, about 3 hr or more.

After the water washing, the tissue may be soaked in a lipid removal solution at a temperature of about 35° C. or more, or about 40° C. more, such as about 44° C. for a soak time of about 3 hr or more, about 4 hr or more, about 5 hr or more. A lipid removal solution may include chloroform, methanol and/or hexane surfactants, chelants and/or buffers, and/or other organic solvents including but not limited to aliphatic solvents, aromatic solvents, carbonyls solvents. Other lipid removal solution or facilitator may be used in the lipid removal process including, but not limited to, a buffer solution used to maintain pH such as Phosphate Buffered Saline (PBS) or Tris Base (base media), a surfactant, such as TritonX-100, Ethylenediaminetetraacetic Acid (EDTA), and Tributyl Phosphate.

The preferred class of lipids targeted during lipid removal includes stratum corneum lipids, sebaceous lipids, and intracellular membrane lipids. Stratum corneum has ceramides, free fatty acids, cholesterol, and cholesterol esters. Sebaceous lipids have squalene, wax esters, triglycerides. Intracellular membrane lipids have glycerophospholipids and glycosphingolipids.

After soaking in lipid removal solution, the tissue may then be water washed with water such as deionized water for about 15 minutes or more at a temperature of about 35° C. or more, or about 40° C. more, such as about 44° C.

After the preceding water washing, the tissue may be soaked in an acid including, but not limited to, acetic, hydrogen peroxide, phosphoric acid, formic acid, or weak acid. A preferred acid solution includes a peracetic acid in a concentration of about a 0.1% peracetic acid and may have a concentration of about 0.1% to about 2%. This soaking in acid may be performed a temperature of about 35° C. or more, or about 40° C. more, such as about 44° C., for about 45 mins or more, about 60 mins or more, about 70 mins or more, about 90 mins or more and any range between and including the time values provided.

After the enzyme soaking, the tissue may then be water washed with water such as deionized water for about 15 minutes or more, such as about 30 minutes or more, at a temperature of 35° C. or more, or about 40° C. more, such as about 44° C.

The tissue may then be soaked in an enzyme solution in DI water at a soak temperature of about 30° C. or more, or about 35° C. more, such as about 37° C. for a soak time of about 8 hr or more, such as from about 8 hours to about 16 hours: The enzyme solution may have the following composition:

a. 2 mM MgCl$_2$
b. 50 mM Tris Buffer
c. 10 KIU/ml aprotinin (enzyme units Kallikrein Inhibitor Unit (KIU)
d. 0.5% Triton X-100
e. 10 U/ml Benzonase
f. pH 8-9.2

After the preceding enzyme soaking, the tissue may then be water washed with water such as deionized water for about 15 minutes or more, such as about 15 minutes or more, at a temperature of 20° C. or more, or about 25° C. more.

Then the tissue may be soaked in progressively higher concentrations of a solvent, such as an organic solvent including, but not limited to, ethanol, methanol, isopropanol, hexanol, and acetone at room temperature. A preferred organic solvent is ethanol. The tissue may be soaked in a first soak of about 70% Ethanol for about two to four hours. The second soaking step may be in 85% Ethanol (RT) for two to four hours. Then the tissue may be soaked in 100% Ethanol for two to four hours at room temperature. The tissue may be soaked again in clean solution of 100% Ethanol for two to four hours at room temperature.

Then the tissue may be soaked in Xylene (RT) for two to four hours.

The ADM as described herein may be used for a number of different purposes including, but not limited to, dermal substitute, skin grafting, abdominal wall reconstruction, hernia repair, rotator cuff, surgical reconstruction, soft tissue repair, and other similar medical applications.

The manufactured dermal scaffold including the manufactured acellular dermal matrix may be shelf stable, as defined hereinafter, as not requiring freeze drying or lyophilization to maintain a dry condition having no more than 20% water when maintained at standard temperature and pressure at less than 50% Rh, for a shelf life of at least 6 months.

The manufactured dermal scaffold including the manufactured acellular dermal matrix may be used for skin reconstruction and may act as a graft for damaged or removed skin, such as from a burn or from an injury or from another medical procedure that requires the removal of skin. Also, the manufactured dermal scaffold including the manufactured acellular dermal matrix may be used for other surgical reconstructions including cosmetic reconstructions.

Definitions

Washing, as used herein, means submerging the ADM or prerequisite to the final ADM in a liquid and may also include agitation of the liquid or solid in the liquid.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 10 shows a table of mechanical data for the ADM of the present invention both dry and hydrated compared with human skin and commercially available ADM.

FIG. 30 shows a process flow diagram for a process to make a manufactured acellular dermal matrix as described herein.

Figure 1:
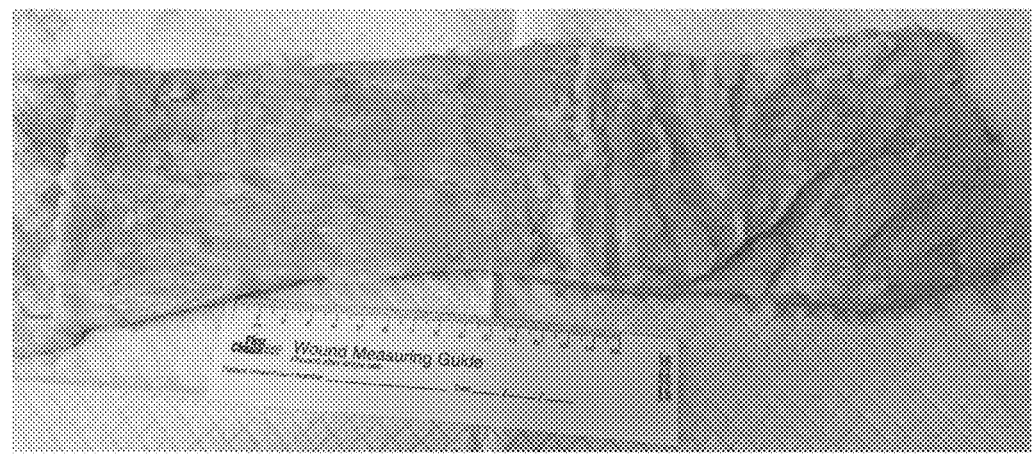
FIG. 1 shows a picture of skin tissue before debridement of fat.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

FIG. 1 shows a picture of skin tissue before debridement of fat.

Figure 2:
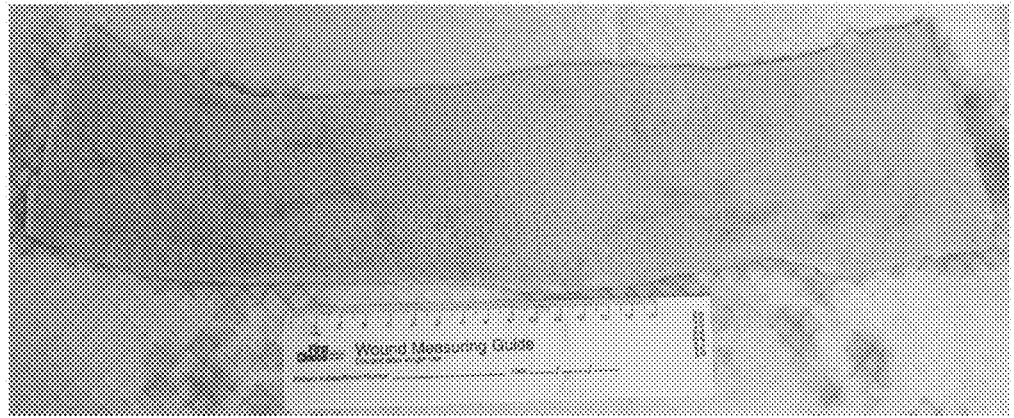
FIG. 2 shows a picture of skin tissue after the debridement of fat.

FIG. 2 shows a picture of skin tissue after the debridement of fat.

Figure 3:
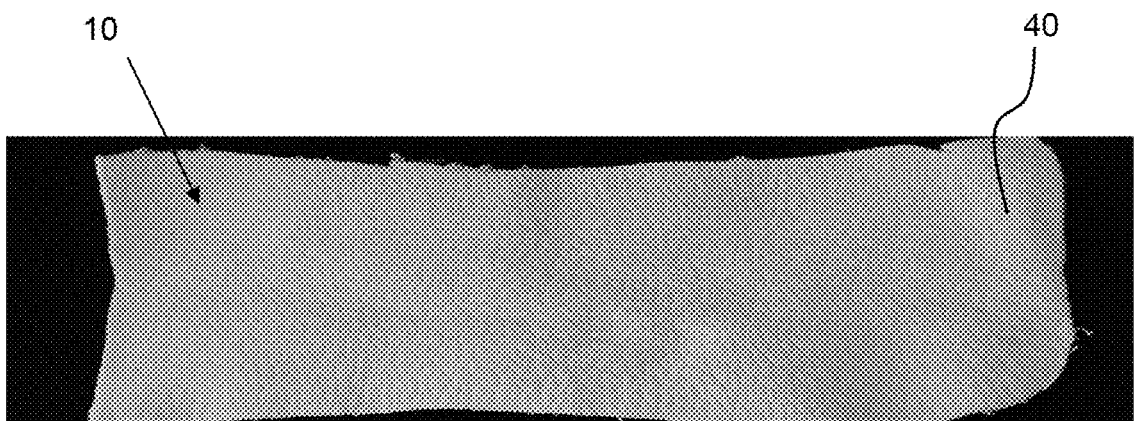
FIG. 3 shows a picture of the ADM of the present invention after processing.

FIG. 3 shows a picture of the manufactured acellular dermal matrix 10 of the present invention after processing. The ADM comprises collagen 40.

Figure 4:
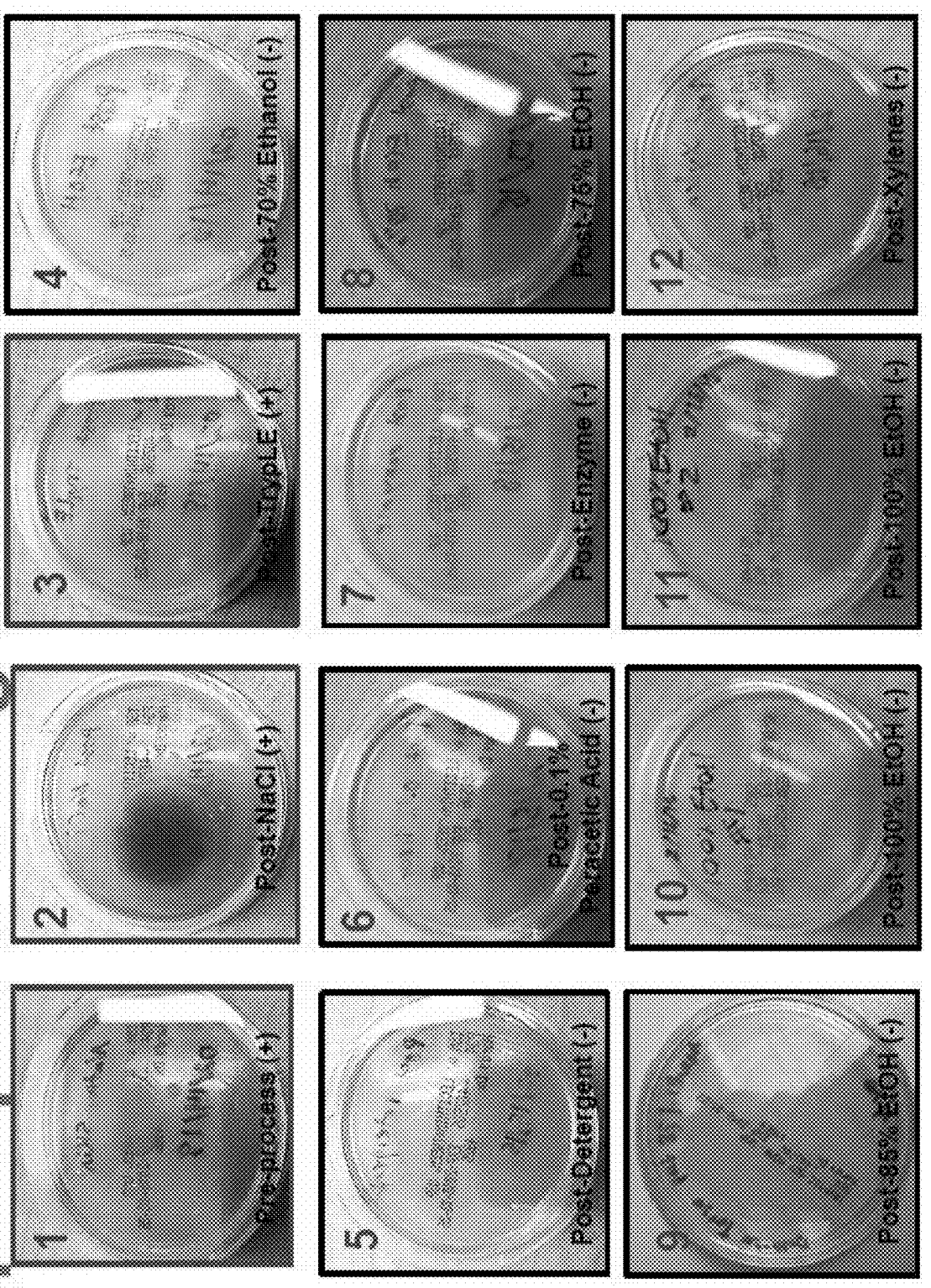
FIG. 4 shows a series of pictures of each stage of the aseptic processing of tissue into acellular dermal matrix of the present invention.

As shown in FIG. 4, swab cultures of the tissue after each step processing step are shown. As shown, native tissue has reduced pathogens as it is processed into an ADM. Each of the images shows the results of a cell culture from a swap taken from the tissue throughout various stages of the process to produce the ADM, wherein:

1) post pre-processing;
   2) post soaking the native tissue in sodium chloride;
   3) post soaking in TrypLE;
   4) post soaking in Ethanol;
   5) post soaking in detergent;
   6) post soaking in Peracetic acid;
   7) post soaking in Enzyme;
   8) post 75% EtOH;
   9) post 85% EtOH;
   10) post 100% EtOH;
   11) post 100% EtOH; and
   12) post Xylene.

Figure 5:
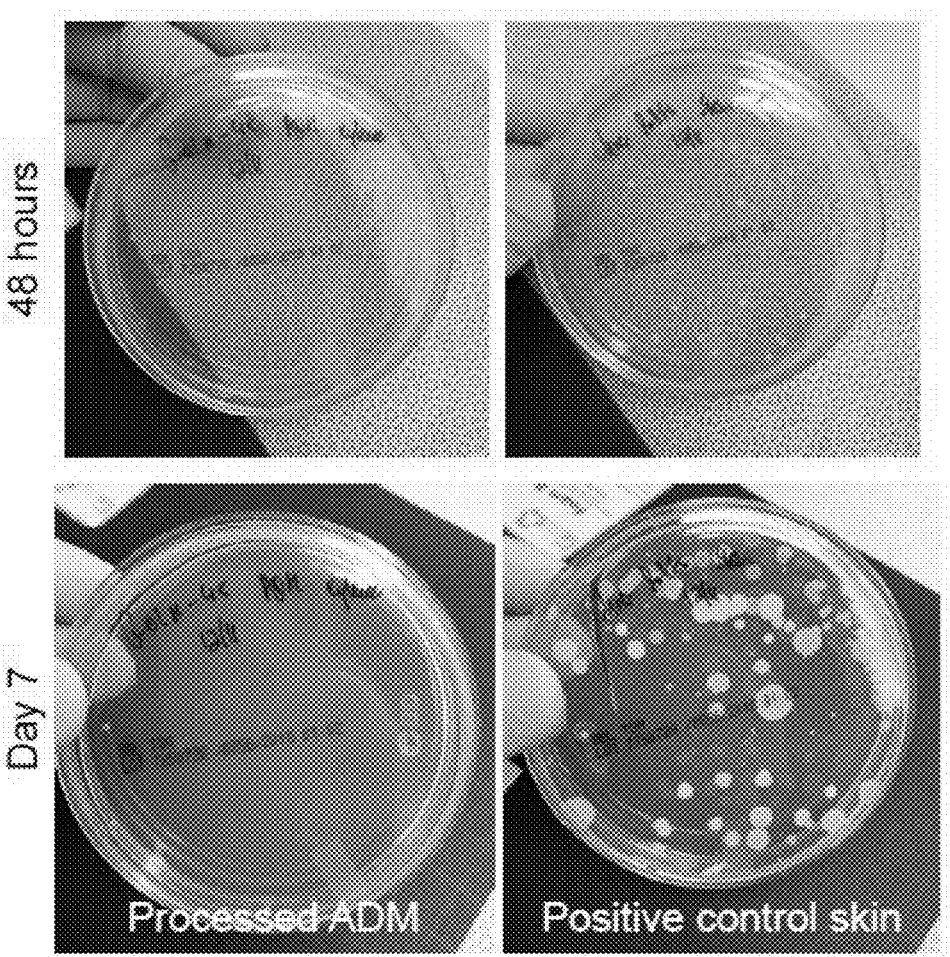
FIG. 5 shows pictures of a swab culture of bacterial growth of the ADM of the present invention and a control skin sample after 48 hours and seven days.

FIG. 5 shows pictures of a culture experiment of the ADM of the present invention and a control skin sample after 48 hours and seven days.

Figures 6, 7:
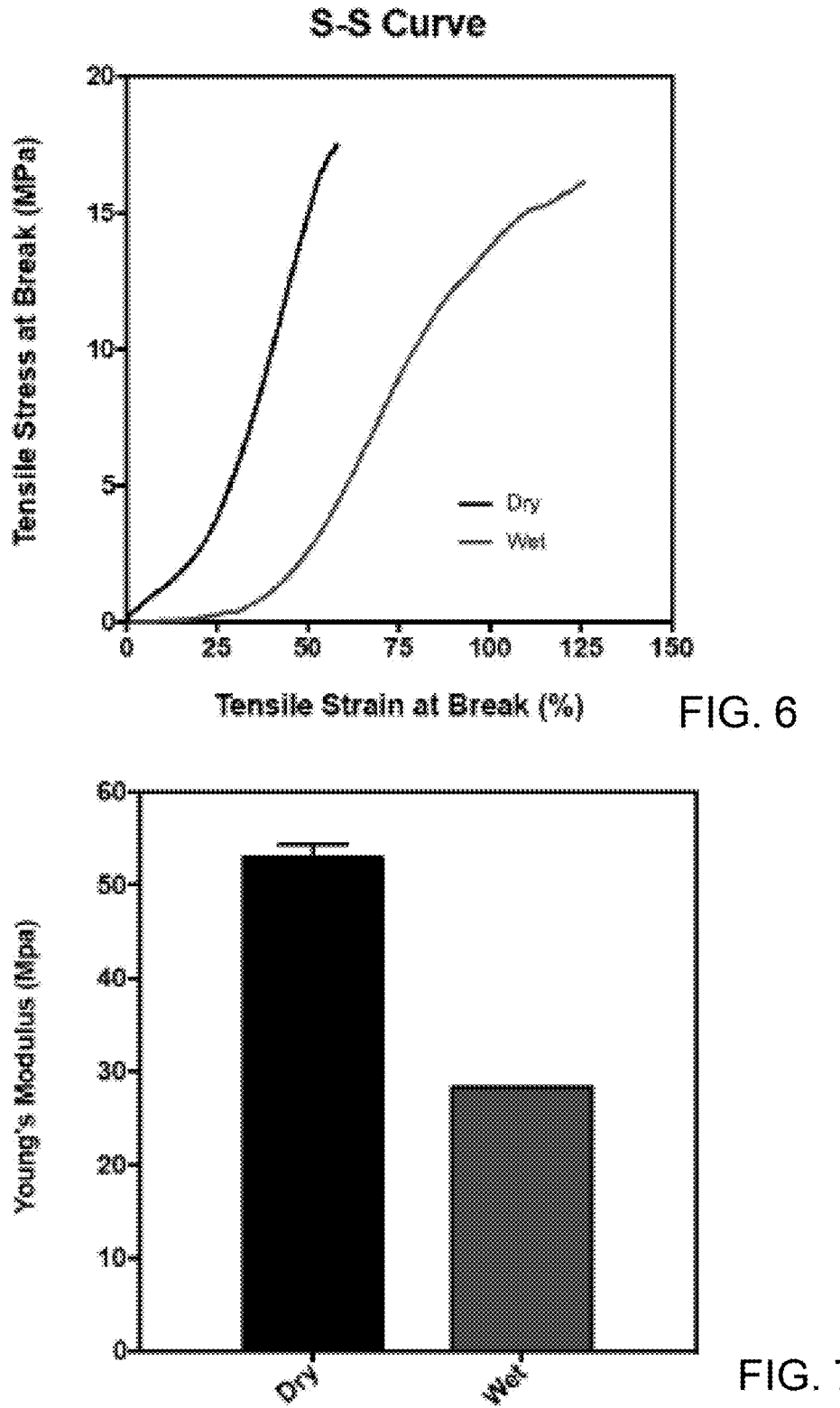
FIG. 6 shows a graph of tensile stress versus tensile strain for dry ADM and hydrated ADM.
FIG. 7 shows a bar graph of Young's modulus for dry ADM and hydrated ADM.

FIG. 6 shows a graph of tensile stress versus tensile strain for ADM and hydrated ADM.

FIG. 7 shows a bar graph of Young's modulus for ADM and hydrated ADM.

Figures 8, 9:
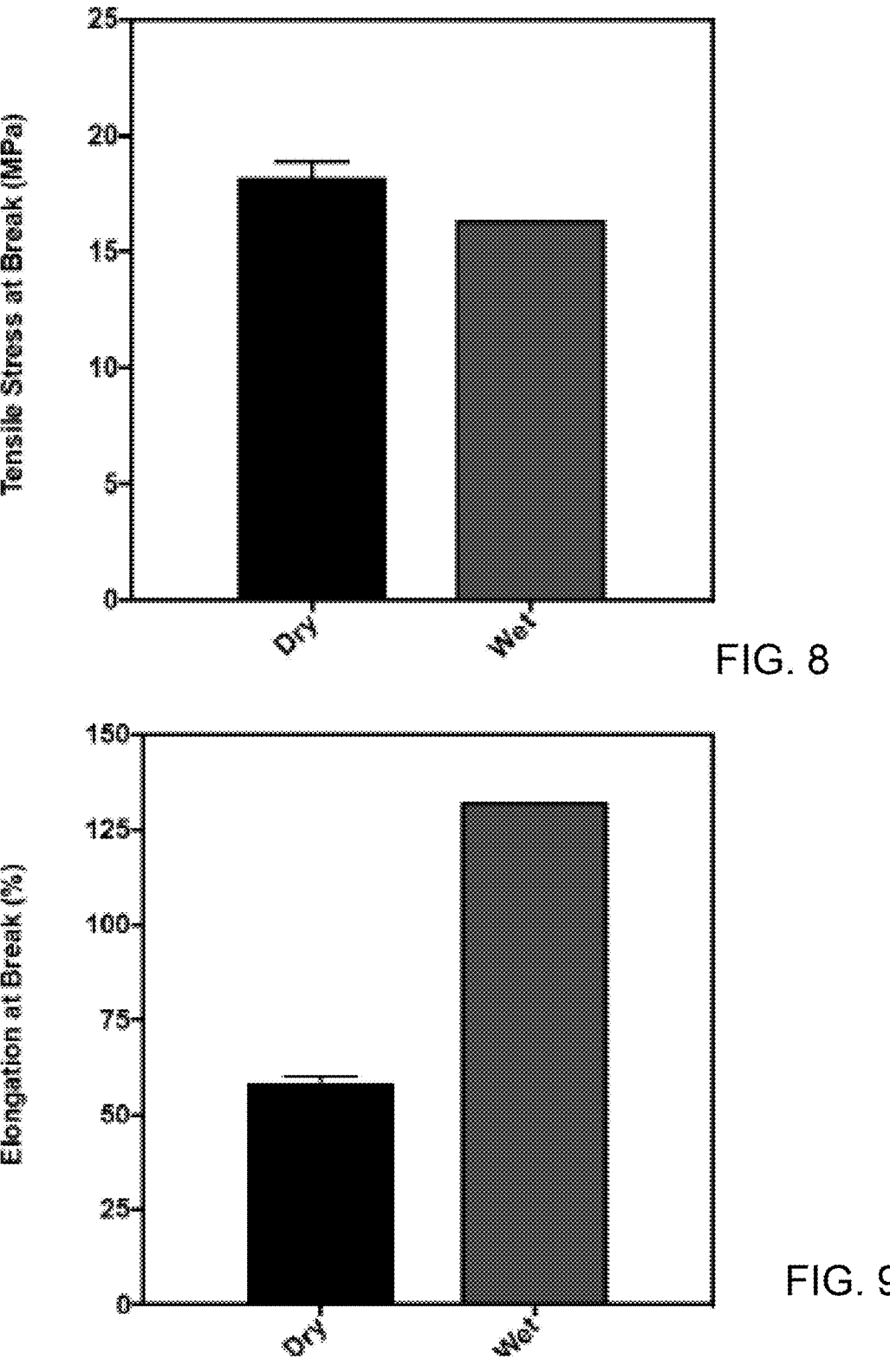
FIG. 8 shows a bar graph of tensile stress at break for dry ADM and hydrated ADM.
FIG. 9 shows a bar graph of elongation at break for dry ADM and hydrated ADM.

Referring now to FIGS. 8 and 9, the ADM shows a rather consistent tensile break strength between wet and dry states. However, the elongation at break is much higher for the wet or hydrated ADM over the dry ADM. In FIG. 8 the tensile stress at break for the dry ADM was about 17.5 MPa and for the wet ADM about 16 for the hydrated ADM. As shown in FIG. 9, the elongation at break for the dry ADM was about 60% and the hydrated ADM Has an elongation at break of about 135%, more than double the elongation at break for the dry ADM. A dry manufactured ADM may have less than 20% moisture, and preferably has less than 15%, as measured using a Thermogravimetric Analyzer (TGA), such as from Fischer Scientific Inc.

FIG. 10 presents a table comparing the mechanical properties of the ADM of the present invention in both dry and hydrated (wet) states to human skin and commercially available ADMs, AlloDerm/FlexHD (MTF Biologics, Edison NJ) and DermaMatrix (Dermamatrix, Sweden) with the latter sourced from the literature. Tensile testing was conducted on both dry and hydrated ADM samples with approximate dimensions of 10 mm×4 mm×2 mm, at a testing rate of 10 mm/min. The results demonstrate that the tensile strength and elastic modulus of the ADM, in both dry and hydrated states, closely match the literature-reported values for human back and abdominal skin and exceed those of other commercially available ADMs. The MPa for the ADM of the present invention was at least 10 MPa or at least 15 MPa and may be from about 10 MPa to about 20 MPa or even 22.5 MPa, and the strain dry was at 50%. Elastic modulus was at least 25 MPa or at least 30 MPa and at least 40 MPa or even at least 50 MPa when dry. Data for the AlloDerm and DermaMatrix was obtained from Gallagher, A. J. Ní Annaidh, Aisling, Bruyère, Karine, et al. The data for human skin was found in the paper entitled Dynamic Tensile Properties of Human Skin, 2012 IRCOBI Conference Proceedings. IRC-12-59. International Research Council on the Biomechanics of Injury, 2012. Available at: http://hdl.handle.net/10197/4772.

Figure 11:
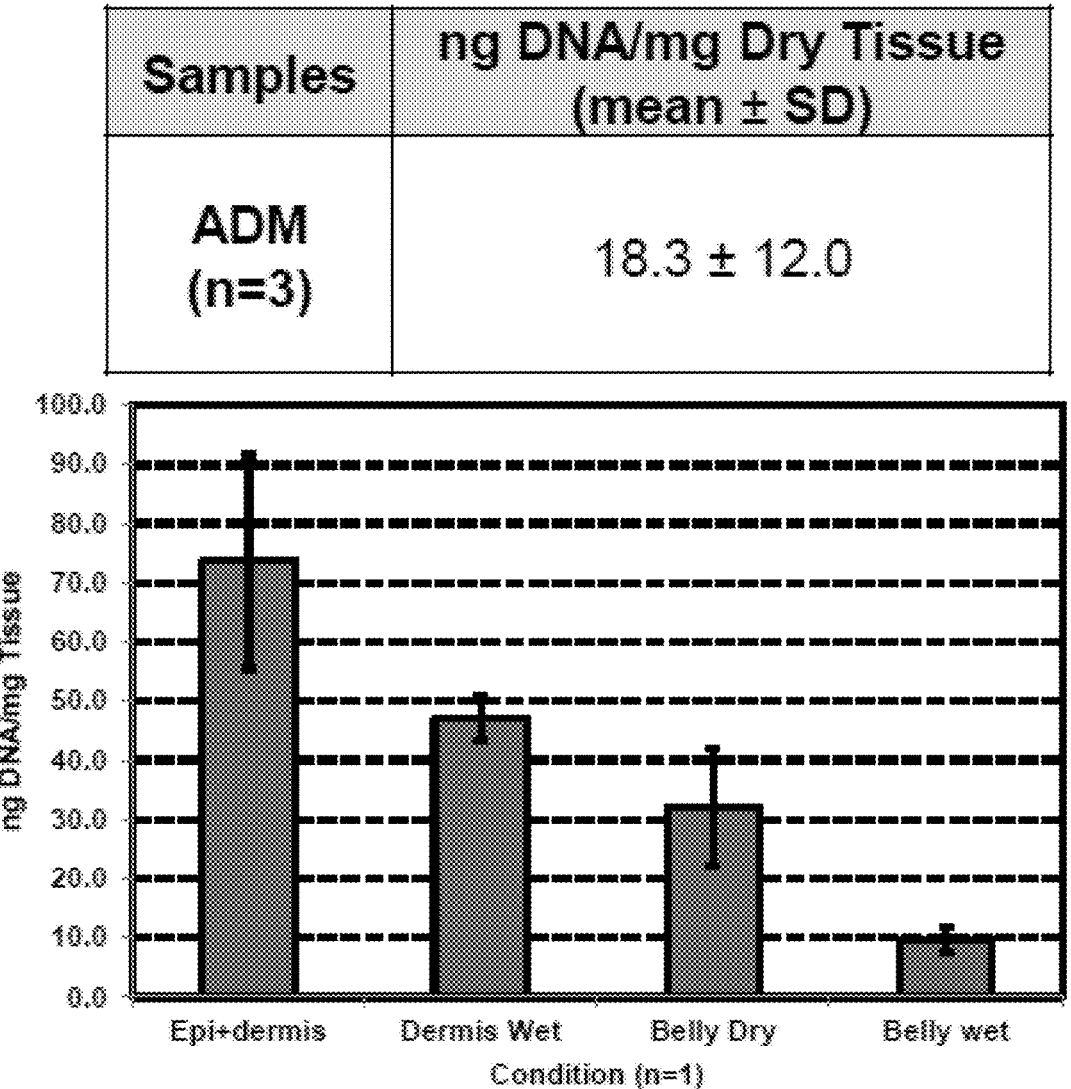
FIG. 11 shows a bar chart of DNA content of dermal tissue.
Figure 12:
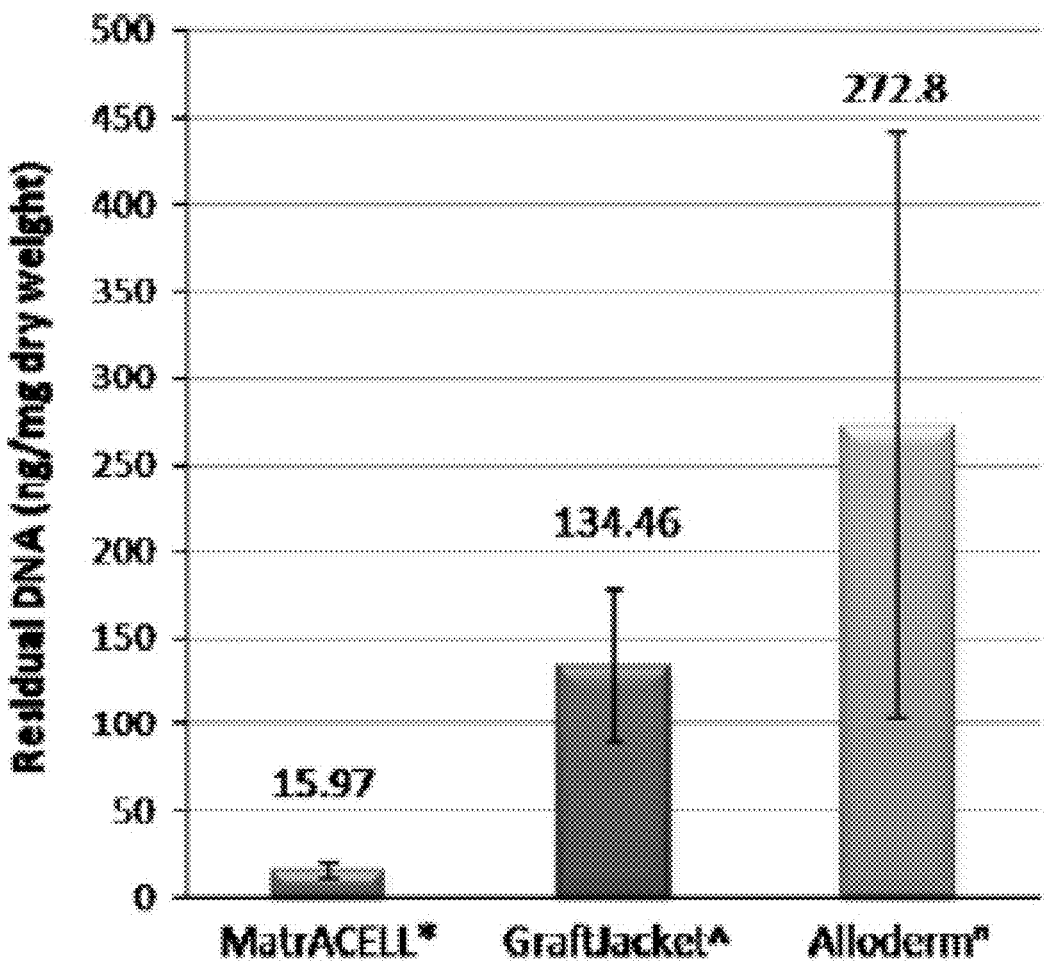
FIG. 12 shows a bar chart of DNA content of commercially available ADM materials.

FIG. 11 shows a bar chart of DNA content of dermal tissue. The DNA content of the ADM was quantified using Quant-iT Picogreen dsDNA kit. Percent DNA removal was calculated by determining the total DNA amount in human tissues prior to processing of ADM using the same method. The results display efficient removal of DNA from the ADM as compared to other commercially available ADM materials shown in FIG. 12. Results based on two fresh donors and on a frozen donor FIG. 12 shows a bar chart of DNA content of commercially available ADM materials. This is a comparison of residual DNA content in three ADM samples. All DNA content results are presented in ng/mg of dry weight of the sample. The MatrACELL data was acquired from the file at LifeNet Health and the GraftJacket data and Alloderm data are from the reported literature. The asterisk on the MatrACELL sample indicates an n of 3 as 1 sample each from 3 donors. GraftJacket sample data is reported in (Derwin et al. 2010) and Alloderm sample data is reported in (Choe and Bell 2001).

Figure 13:
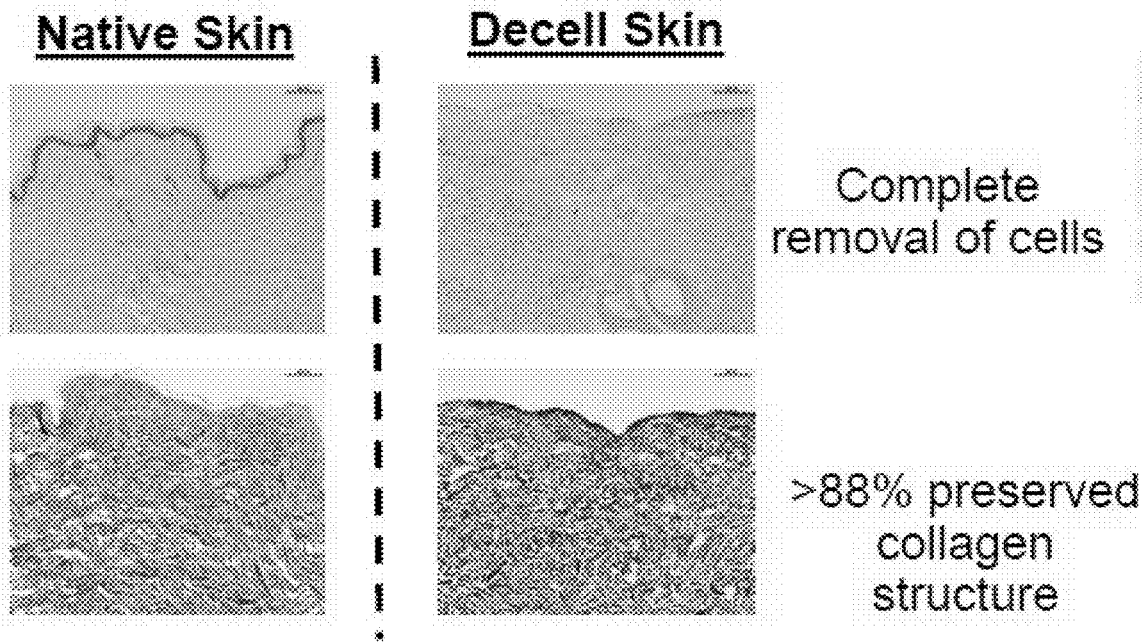
FIG. 13 shows slide images from histology of native skin tissue and decellularized skin tissue.

FIG. 13 shows slide images from histology of native skin tissue and decellularized skin tissue. Collagen is preserved through the decellularization process. A histologist compares a slide of the tissue pre and post the decellularization process to determine a percentage of collagen that is preserved.

Figure 14:
FIG. 14 shows a histology stain of blood vessel in the decellularized skin tissue after implantation.
Figure 15:
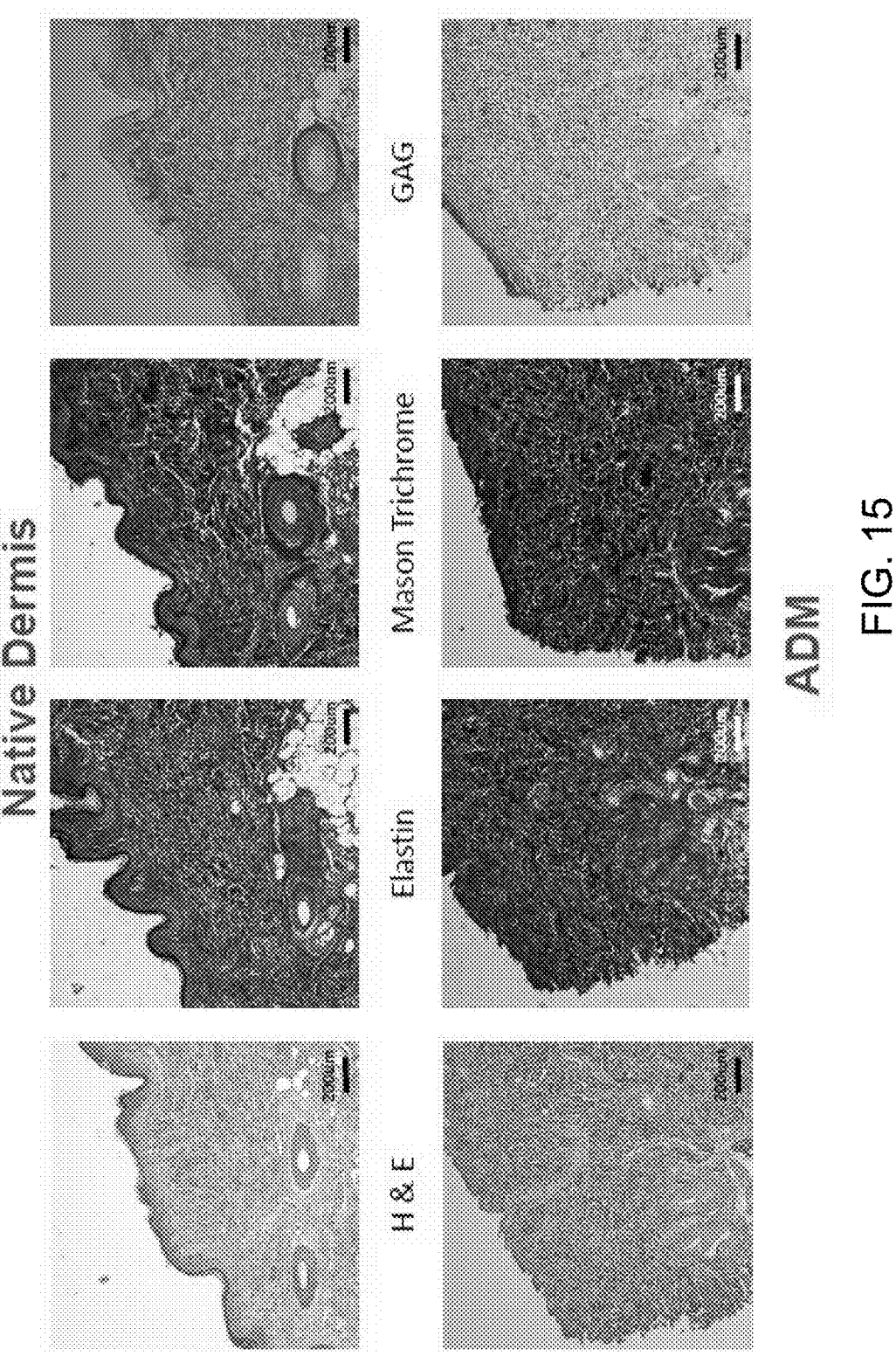
FIGS. 15 to 19 show slide image from histology of skin tissue versus ADM of the present invention.

FIG. 14 shows that during decellularization does not damage the tissue as evidenced by this intact blood vessel. The collagen is not damaged during the decellularization process.

FIGS. 15 to 19 show slide image from histology of skin tissue versus ADM of the present invention.

Figure 16:
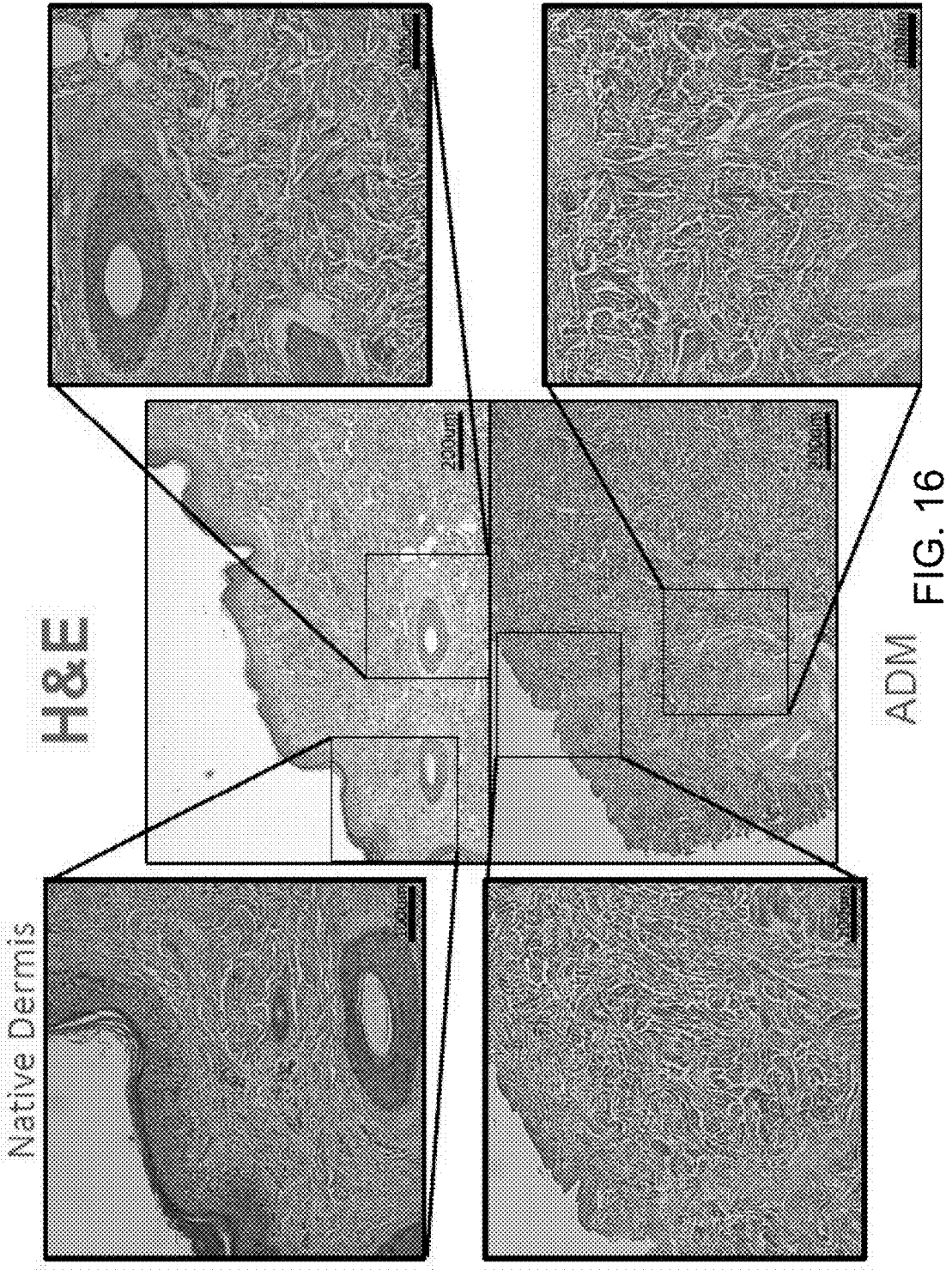

FIG. 16 demonstrates the efficient decellularization of the acellular dermal matrix ADM compared to native dermis using hematoxylin and eosin (H&E) staining. The images reveal the absence of cellular components in the ADM while preserving the overall tissue architecture.

Figure 17:
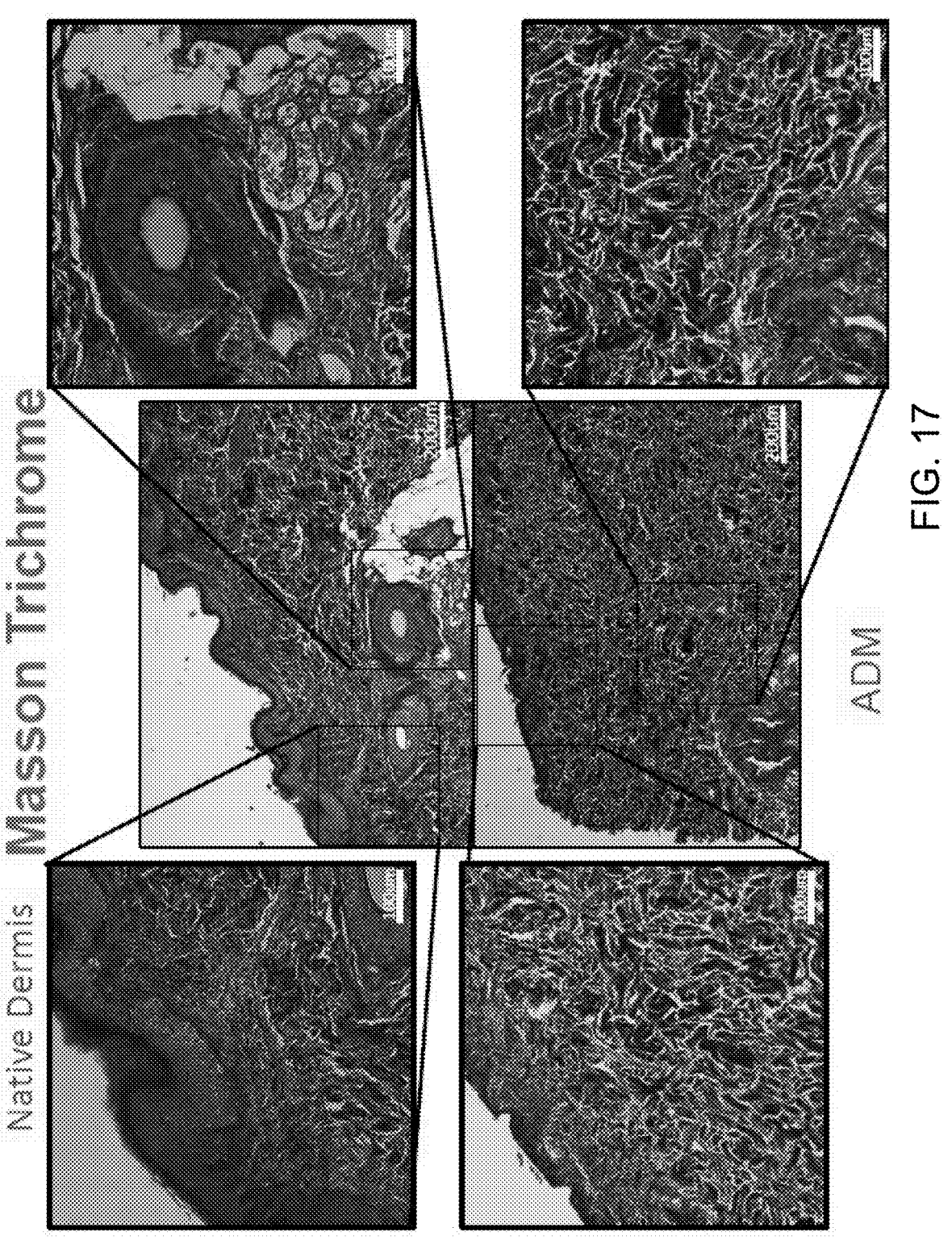

FIG. 17 demonstrates the collagen fibers and structure of ADM compared to native dermis, using Masson's Trichrome staining. The ADM shows an intact collagen architecture following the decellularization process, with well-preserved collagen fibers similar to those found in the native dermis. Both the ADM and native dermis exhibit a dense collagen matrix, indicating that the decellularization process did not disrupt the collagen structure. This intact collagen architecture in ADM mirrors that of the native dermis, suggesting its potential as a viable substitute in regenerative applications where collagen integrity is essential for tissue function.

Figure 18:
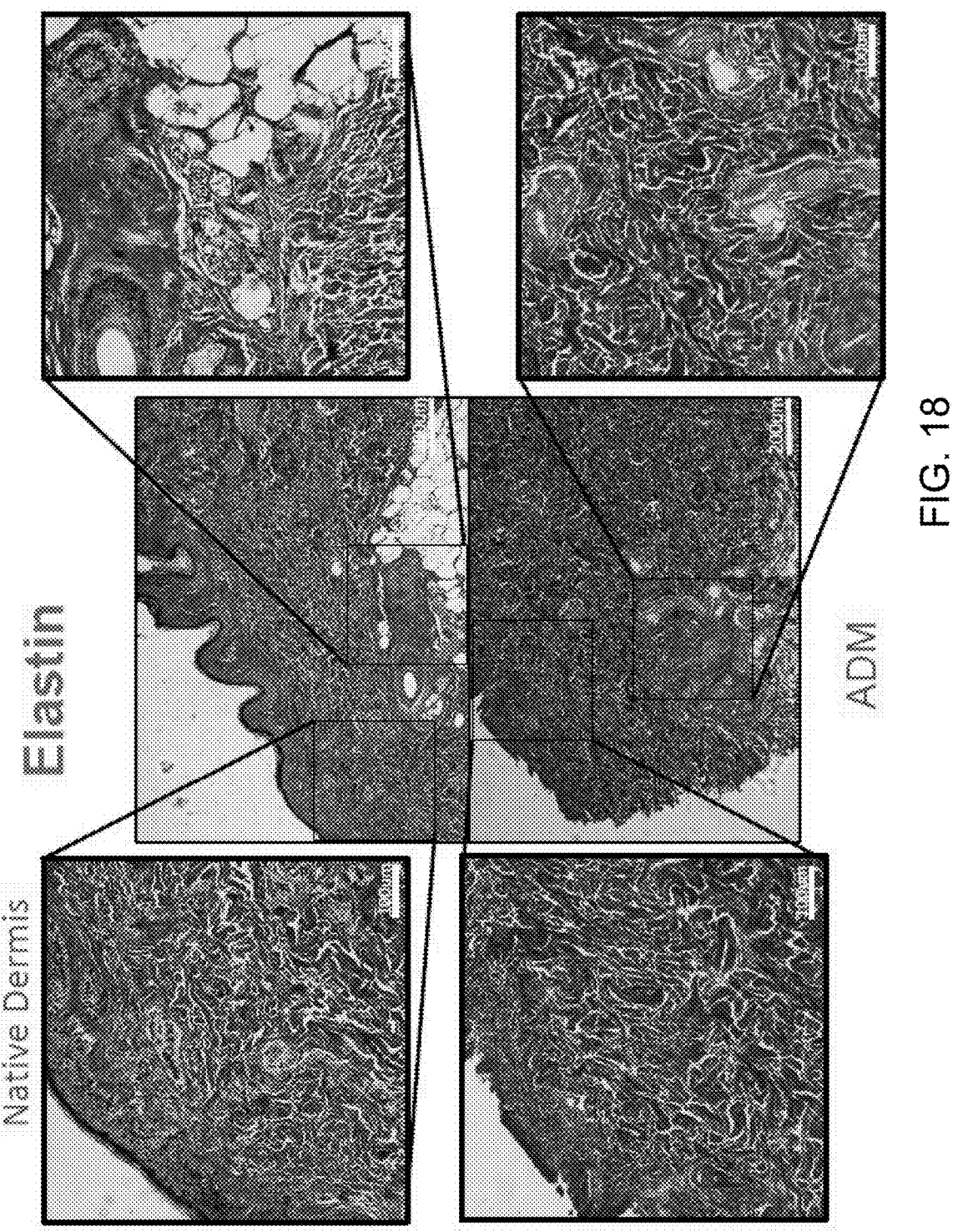

FIG. 18 utilizes Verhoeff-Van Gieson staining to confirm the preservation of elastin protein in the ADM following decellularization. The stain highlights the presence of elastin fibers within the ADM, demonstrating that the elastin content is well-preserved and retained after the decellularization process. This confirms that the decellularization procedure did not adversely affect the elastin matrix, which is critical for maintaining the tissue's elasticity and functional properties.

Figure 19:
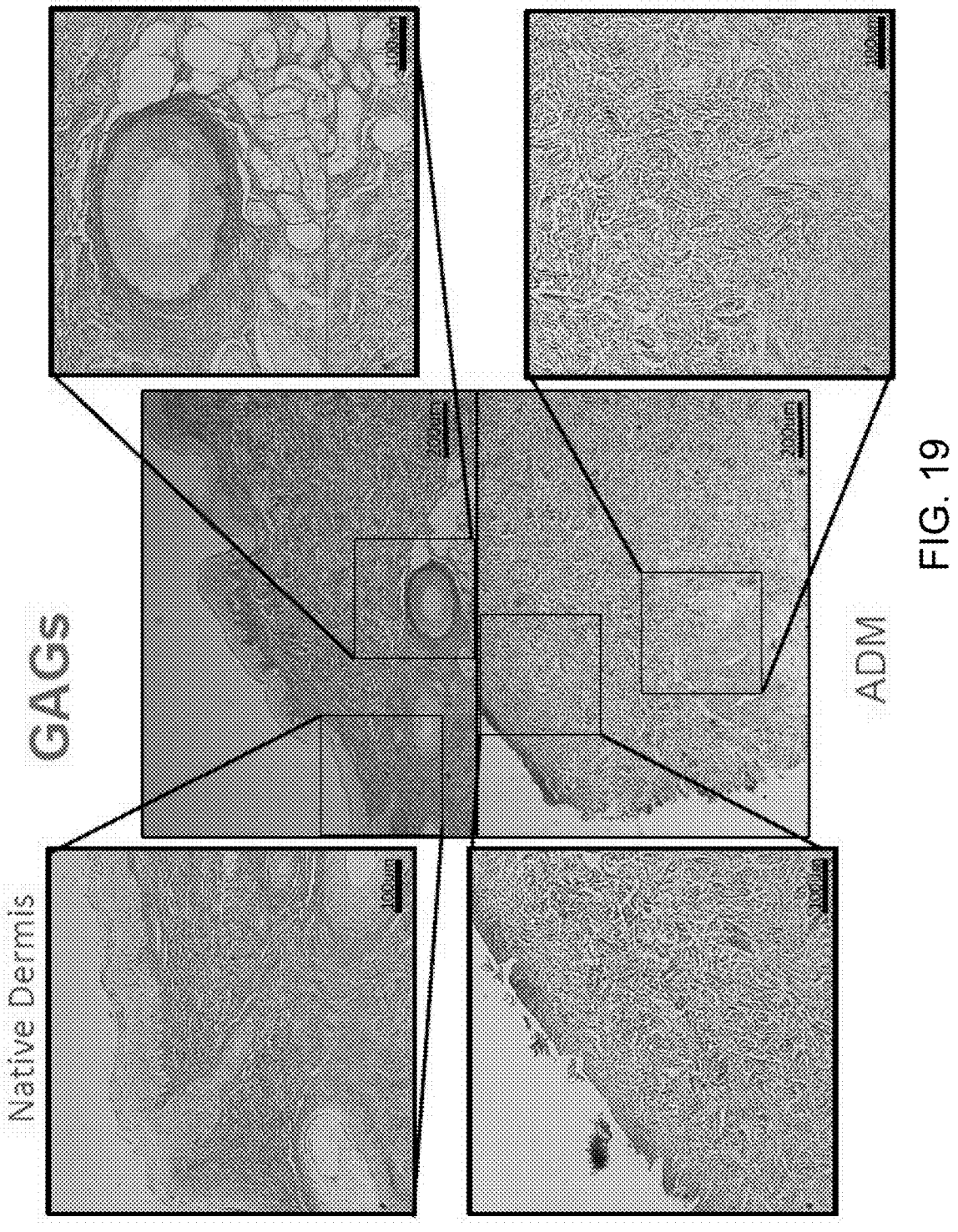

FIG. 19 shows slide images of Alcian Blue staining to detect glycosaminoglycans (GAGs) in the ADM. The staining reveals that GAGs are well-preserved in the ADM, with a similar distribution pattern to that observed in the native dermis. This indicates that the decellularization process did not significantly alter the GAG content, which is crucial for maintaining the tissue's hydration, elasticity, and overall extracellular matrix integrity.

Figure 20:
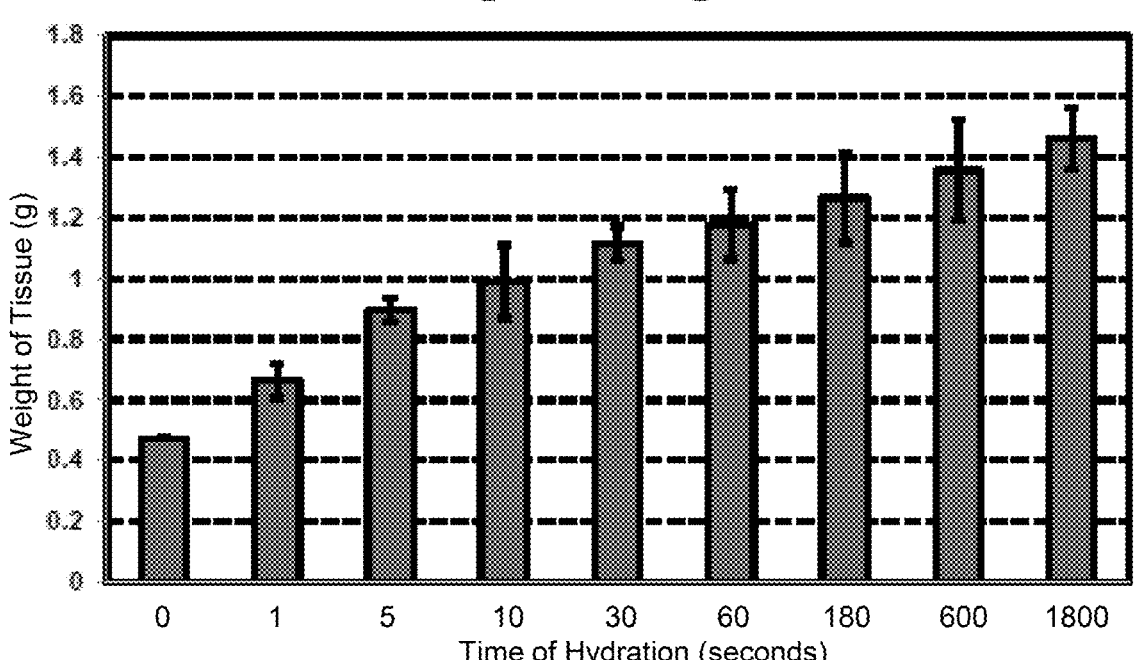
FIG. 20 shows a bar graph of weight of ADM versus time of hydration.

FIG. 20 shows a bar graph of weight of ADM versus time of hydration. As shown, the weight of the ADM doubles in 5 seconds and about triples in 60 seconds. The tests were performed at ambient conditions. The sample was placed into a saline solution and then removed and weighed. The material has a thickness change from dry to wet of no more than 75% no more than 65%, no more than 50%. A hydration rate is the time to double in weight when soaked in water at room temperature and may be about 60 seconds or less, about 30 seconds or less, about 10 seconds or less or even about 7 seconds or 5 seconds or less.

Figure 21:
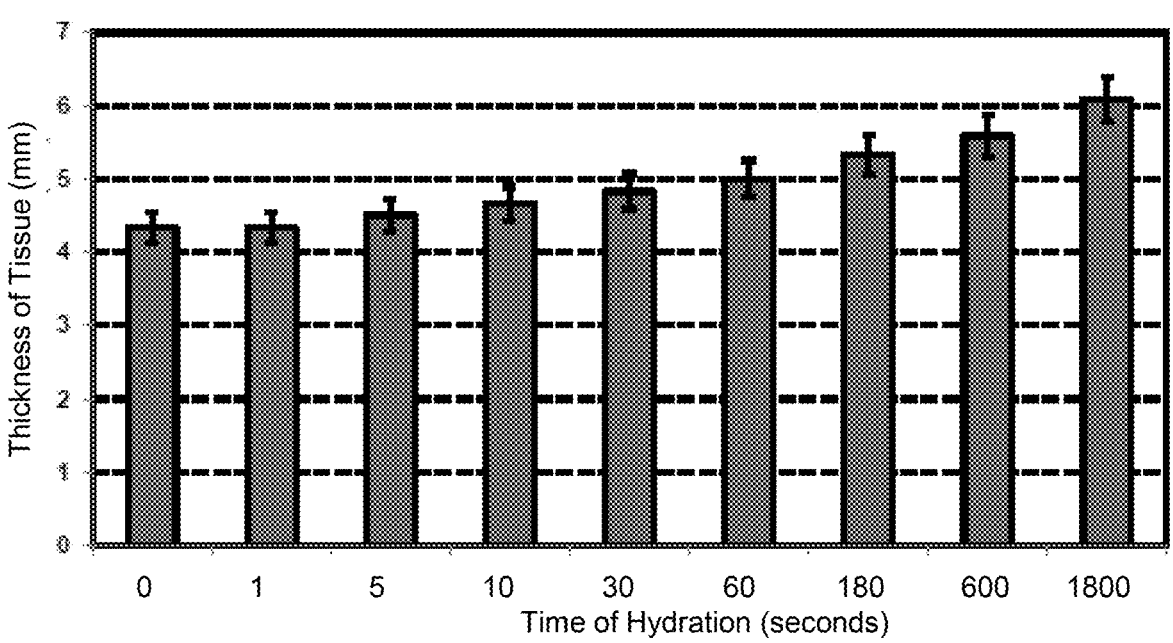
FIG. 21 shows a bar graph of thickness of ADM versus time of hydration.

FIG. 21 shows a bar graph of thickness of ADM versus time of hydration. As shown, the thickness increases much less than the weight gain, wherein the increase in thickness after 60 seconds is about 25% or less, wherein the thickness increase after 30 seconds is about 25% or less, and after 10 seconds was about 15% or less. A combination of hydration rate of less than 30 seconds with a thickness of less than 25% is a valuable combination of performance properties for many applications.

Figure 22:
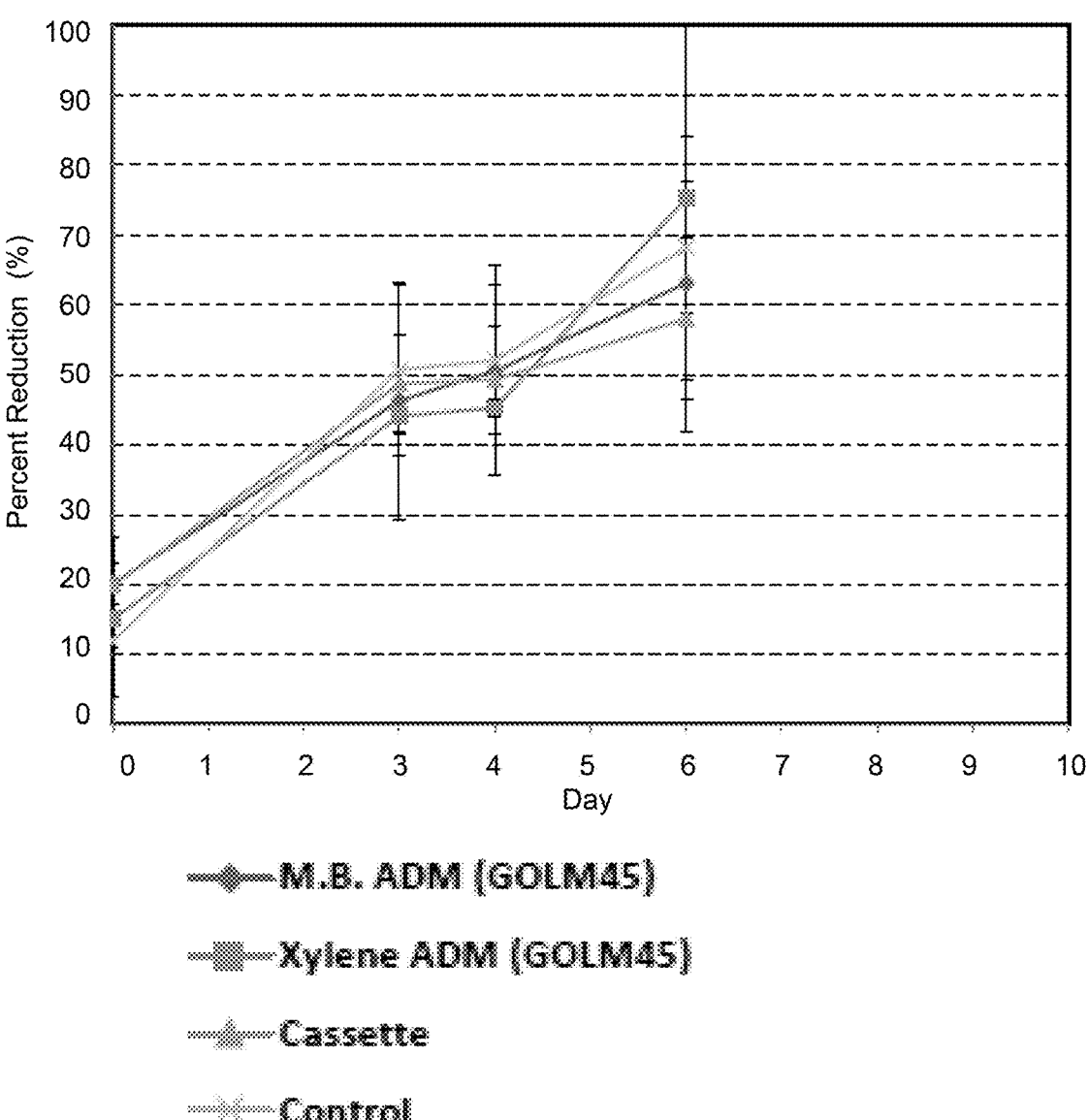
FIG. 22 shows a graph of ADM effect on fibroblast growth.

FIG. 22 presents the results of a leaching study designed to assess whether any substances leached from the acellular dermal matrix (ADM) could inhibit fibroblast growth. In this study, fibroblasts were cultured, and ADM samples treated with different chemical agents were introduced to the culture. If the ADM released harmful compounds, fibroblast proliferation would be reduced. Cell metabolic activity was measured based on fluorescence intensity using alamarBlue assay. A higher fluorescence signal corresponds to greater cell activity and proliferation. This study assesses the impact of chemical treatments on acellular dermal matrix (ADM) by evaluating the effect of leached substances on fibroblast growth. ADM samples are treated with different chemicals, and the resulting leachates are introduced to fibroblast cultures by incubating the fibroblasts with the treated ADM in the same culture plate. The alamarBlue assay is used to measure fibroblast proliferation, determining the inhibitory effects of leached compounds on cell viability.

The study found that xylene-treated ADM exhibited the lowest reduction in fibroblast growth, followed by the control, methyl benzoate, (M.B. ADM) and cassette-treated ADM, which showed the highest reduction in proliferation. The dye in the alamarBlue assay undergoes a reduction reaction in metabolically active cells, producing a measurable fluorescence signal. A decrease in fluorescence intensity indicates fewer viable cells, suggesting potential cytotoxic effects from leached substances. The percentage reduction in fluorescence provides a quantitative measure of the impact of leached compounds on fibroblast viability.

Figure 23:
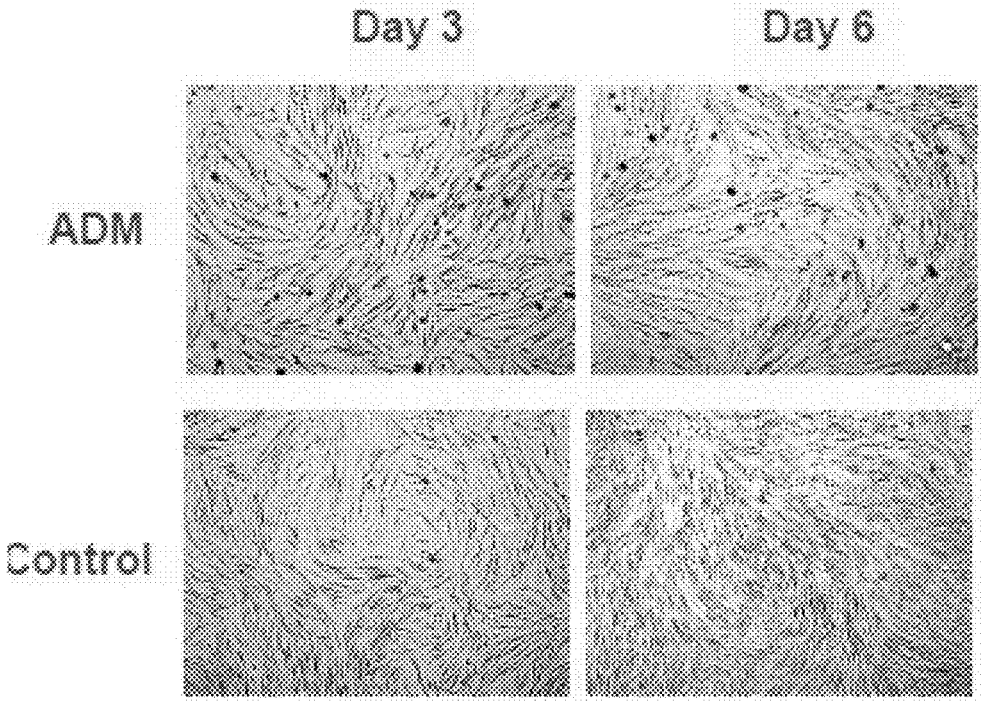
FIG. 23 shows brightfield images illustrating fibroblast attachment and proliferation in the presence of xylene-treated ADM compared to the control (tissue culture plate), captured on day 3 and day 6 post-seeding.

FIG. 23 shows brightfield images illustrating fibroblast attachment and proliferation in the presence of xylene-treated ADM compared to the control (tissue culture plate), captured on day 3 and day 6 post-seeding. This test shows that there are no significant changes in the cell attachment and proliferation between the control and the test sample, therefore the sample did not leach out any toxic reagents that would affect the cells. This test demonstrates that the ADM is biocompatible.

Figure 24:
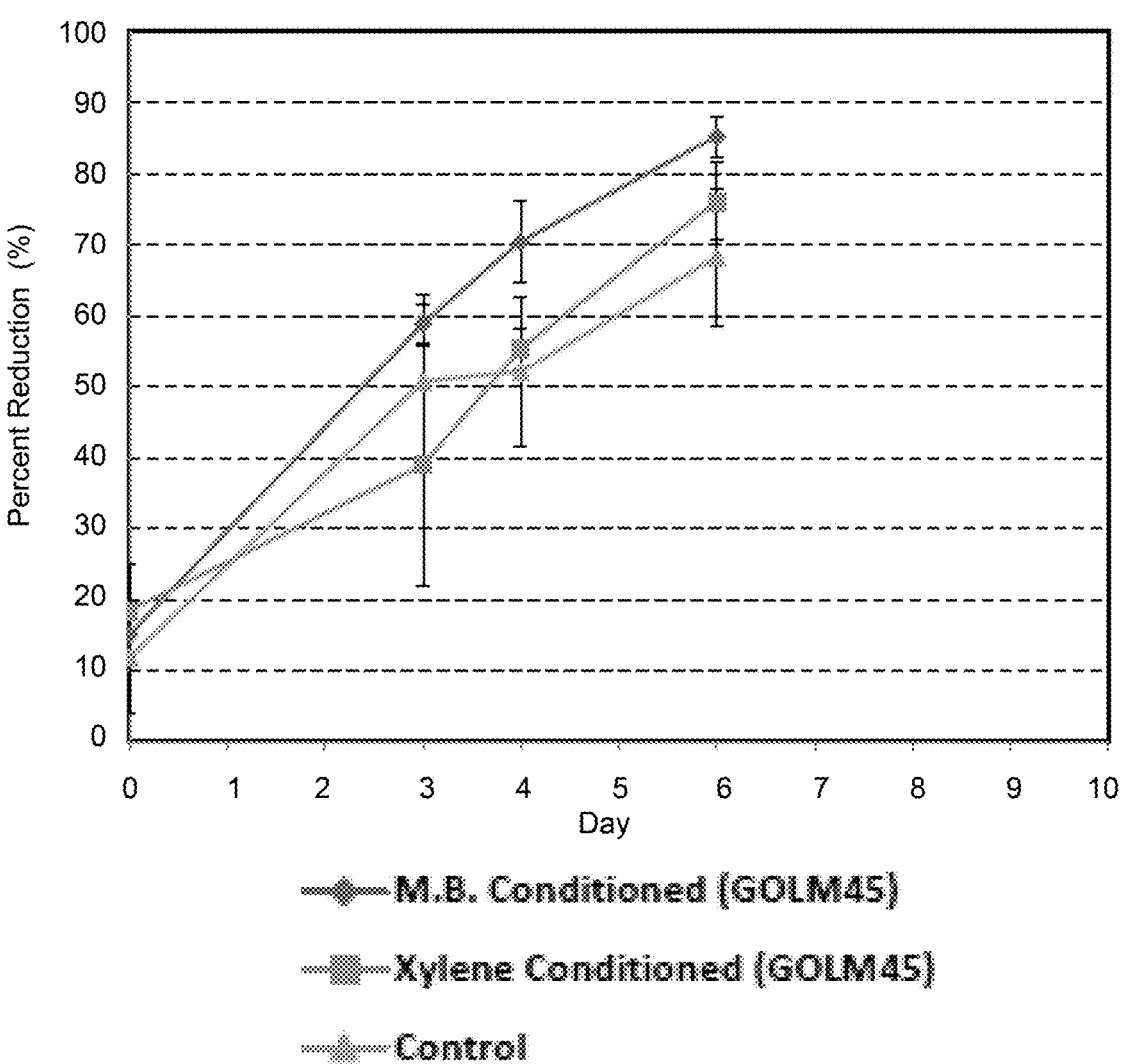
FIG. 24 shows a graph of the percentage reduction in fibroblast growth when fibroblasts are cultured in conditioned media containing xylene and methyl benzoate.

FIG. 24 presents the results of a leaching study to evaluate the potential cytotoxic effects of xylene and methyl benzoate on fibroblast proliferation when these chemicals are present in the culture media. In this experiment, fibroblasts were cultured in normal conditions in the presence of ADM treated with xylene or methyl benzoate as part of processing steps. The treated ADMs were present in the culture plate allowing xylene or methyl benzoate to leach out of the ADM into the culture media that is used to grow the fibroblasts. The ADM was put in the cell culture media for about 5 days to enable leaching from the ADM into the cell culture media. The cell culture plates were at 37° C. and 5% $CO_2$ cell culture incubator. The alamarBlue assay was used to assess cell metabolic activity, where higher fluorescence intensity indicates greater proliferation. The data showed that there is no significant difference in the reduction of fibroblast growth between methyl benzoate-containing media, xylene-containing media, and untreated control. The assay's fluorescent output provides a quantitative measure of how the presence of leached substances in the media influences fibroblast viability and metabolic activity.

Figure 25:
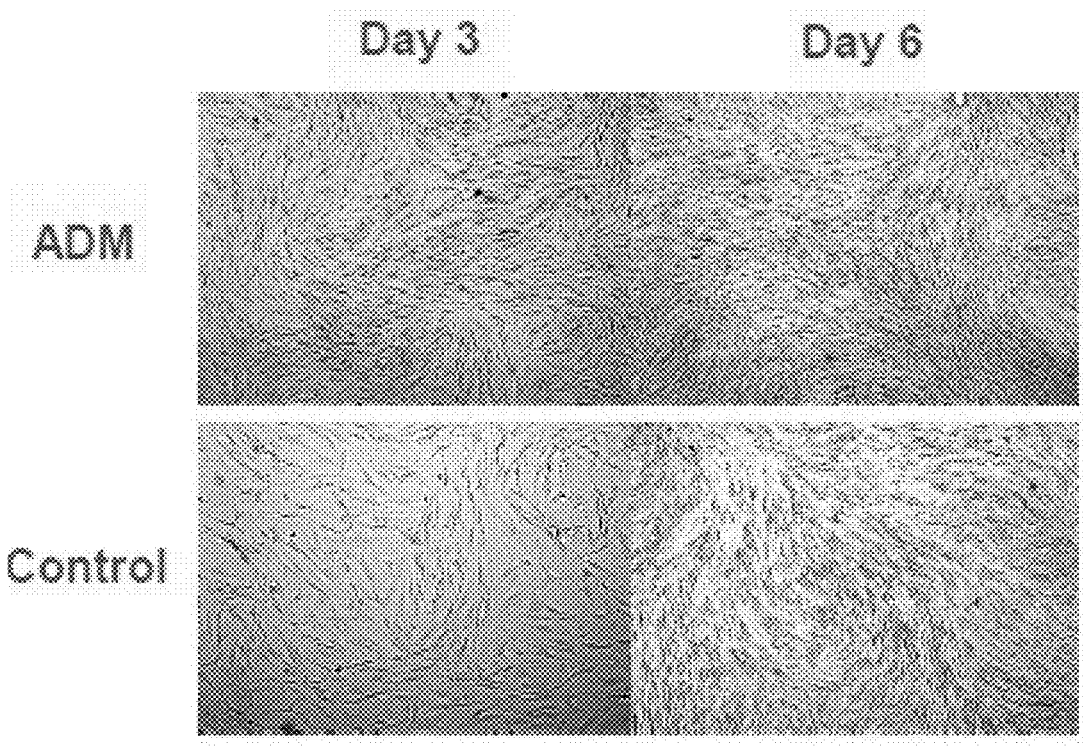
FIG. 25 shows brightfield images demonstrating fibroblast attachment and proliferation on tissue-culture plate when fibroblasts are cultured in conditioned media containing xylene and methyl benzoate leached from ADM, compared to the untreated control, captured on day 3 and day 6 post-seeding.

FIG. 25 shows brightfield images of fibroblasts cultured in conditioned media containing xylene. The ADM was washed in conditioned media for a minimum of 5 days allowing xylene to leach out of the ADM. The ADM was previously treated with xylene as part of the processing steps. The conditioned media containing leached xylene was compared to an untreated control, with images captured on day 3 and day 6 post-seeding. The fibroblasts exhibited comparable attachment and proliferation in both xylene-conditioned media and control media, with no noticeable differences in cell morphology or confluence. These observations indicate that xylene-conditioned media does not adversely affect fibroblast viability or behavior, supporting the conclusion that no cytotoxic substances were leached from the ADM during xylene treatment. This further confirms the biocompatibility of the ADM under the tested conditions.

Figure 26:
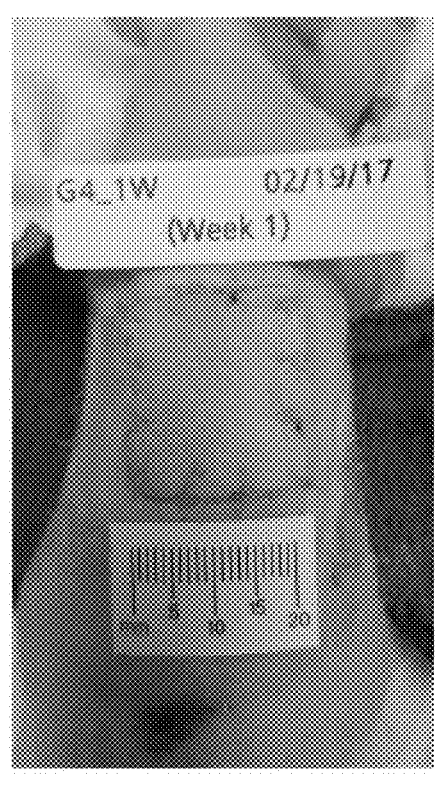
FIG. 26 shows a picture of the ADM sutured onto the skin of a mouse, with the image captured one-week post-suturing.
Figure 27:
FIG. 27 shows a picture of the vascularization observed on the ADM from FIG. 26, at the site of suturing.

FIG. 26 shows that an implantation study was conducted where the ADM was sutured onto the skin of a mouse, with the image captured one-week post-suturing. In addition, FIG. 27 highlights vascularization observed on the ADM at the suturing site. Referring now to FIGS. 26 and 27, an implantation study included an attachment of an ADM of the present invention to the back of a mouse. FIG. 26 shows the ADM sutured onto the skin of a mouse, with the image captured one-week post-suturing. FIG. 27 shows vascularization observed on the ADM at the site of suturing.

Figure 28:
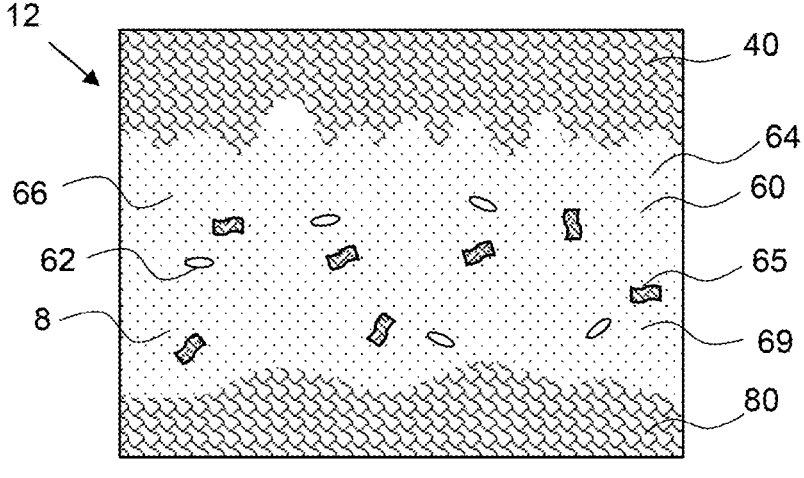
FIG. 28 shows a cross-sectional view of skin tissue.

As shown in FIG. 28, the mammalian skin tissue 12 comprises epidermis 40, dermis 60, hypodermis 80. Also, the mammalian skin tissue 12, such as in the dermis 60, may include fibroblast 65, collagen 64, proteins 66, cells 62, elastin 69 and DNA 8. The proteins may include glycoproteins, and lipids. The mammalian skin tissue may also include collagen, proteins including glycoproteins, lipids, genetic material including DNA, cells with a cell membrane and an extracellular matrix.

Figure 29:
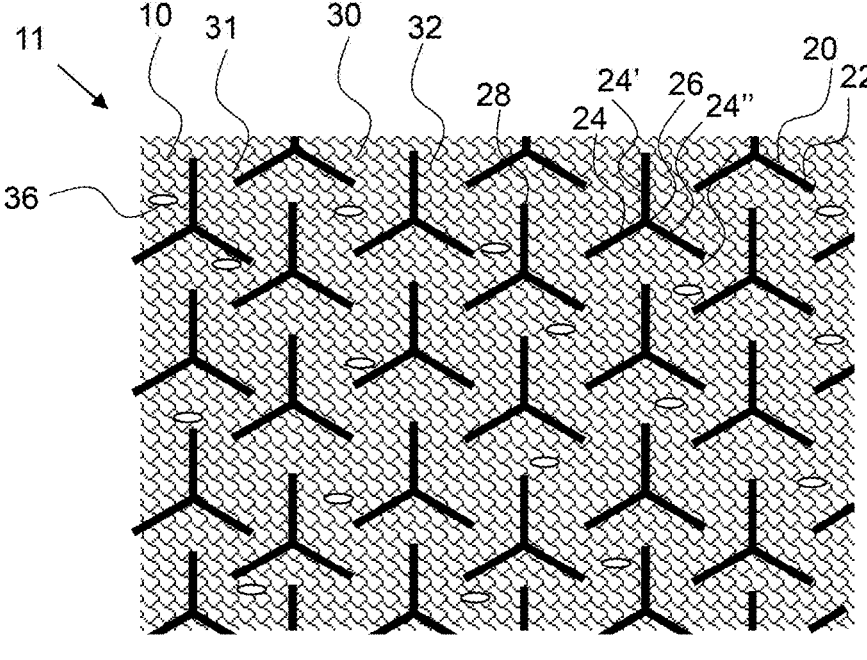
FIG. 29 shows a top view of a manufactured dermal scaffold that includes a manufactured acellular dermal matrix having a plurality of apertures that form an aperture pattern.

As shown in FIG. 29, a manufactured dermal scaffold 11 includes a manufactured acellular dermal matrix 10 that has a plurality of apertures 20 that form an aperture pattern 22. The apertures may include elongated apertures 24, 24', 24", and the elongated apertures may form interconnected elongated apertures, wherein two or more elongated apertures are interconnected by nodes 26, an intersection of two or more elongated apertures. The elongated apertures may extend from the node at an offset angle to each other, such as between about 10 to 170 degrees to form interconnected elongated apertures 28. An elongated aperture may have a length that is at least three times a width and may be a slit. Apertures may be formed by a mesher, a device that is commonly used in a procedure facility such as an operating room to produce an aperture pattern in tissue.

Also shown in FIG. 29 the manufactured dermal scaffold 11 includes a manufactured acellular dermal matrix 10 (ADM) that may include a medicant 30, such as an antibiotic, an anti-inflammatory medicant, a coagulant and the like. Also, the manufactured dermal scaffold 11 may include additional materials such as biological materials 31 to promote wound healing, such as growth factors 32 and/or cells 36 that may be added to the acellular dermal matrix. The cells may be from another source than the mammalian tissue that was used to make the manufactured ADM.

As shown in FIG. 30, a process flow diagram details an exemplary process to make acellular dermal matrix. A mammalian skin tissue is first washed with an ionic solution at a concentration of 1M or more at a temperature of 40° C. or higher for at least 3 hours to disrupt the cell membranes and produce an epidermis free tissue. The ionic solution may be sodium chloride solution as this is preferred due to the accessibility and low cost. Then the epidermis free tissue is exposed to a recombinant serine protease enzyme to destroy the cells while preserving the extracellular matrix to produce a processed dermal tissue. The cells are made non-viable, thereby destroying the cell. A non-viable cell is a destroyed cell as used herein. Then the residual lipids are removed from the processed dermal tissue using an organic solvent or surfactant-based solution containing one or more of chloroform, methanol, hexane, or surfactants to produce a lipid extracted tissue. Then the lipid extracted tissue is treated with an acid solution containing 0.01% to 2% peracetic acid for at least 45 minutes to achieve microbial inactivation to produce a microbe-free ADM. Then the microbe-free ADM is subject to a dehydration step using a solution containing one or more of ethanol, methanol, acetone, or xylene to produce a manufactured acellular dermal matrix.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention covers the modifications, combinations and variations of this invention provided they come within the scope of the appended claims and their equivalents.

What is claimed is:

1. A method of making the manufactured acellular dermal matrix, said method comprising:

a) providing a mammalian skin tissue comprising:
  i) a collagen;
  ii) proteins including glycoproteins, and lipids;
  iii) genetic material including DNA;
  iv) cells with a cell membrane; and
  v) extracellular matrix;

b) disrupting the cell membranes of the mammalian skin tissue by washing the mammalian skin tissue with an ionic solution at a concentration of 1M or more at a temperature of 40° C. or higher for at least 3 hours to disrupt the cell membranes and produce an epidermis free tissue;

c) washing the epidermis free tissue in a recombinant serine protease enzyme to destroy the cells while preserving the extracellular matrix to produce a processed dermal tissue;

d) removing residual lipids from the processed dermal tissue using an organic solvent or surfactant-based solution containing one or more of chloroform, methanol, hexane, or surfactants to produce a lipid extracted tissue;

e) washing the lipid extracted tissue with an acid solution containing 0.01% to 2% peracetic acid for at least 45 minutes to achieve microbial inactivation to produce a microbe-free acellular dermal matrix; and f) dehydrating the microbe-free acellular dermal matrix by washing the microbe-free acellular dermal matrix in a dehydration solution containing one or more of ethanol, methanol and acetone, and subsequently washing in xylene to selectively remove cellular debris and membrane lipids without disrupting collagen fiber organization to produce the manufactured acellular dermal matrix comprising:
  i) at least 70% of the collagen;
  ii) no more than 20 ng DNA/mg of the manufactured acellular dermal matrix;
  iii) a solvent concentration of no more than 10 mg/g of manufactured acellular dermal matrix;
  iv) a hydration rate, a time to double in weight when the manufactured acellular dermal matrix is soaked in water, of no more than 60 second;
  v) an elongation at break when said manufactured acellular dermal matrix is a hydrated acellular dermal matrix of 50% or more as determined by a tensile test with a 25.4 mm (1 in) jaw gap and strain rate of 10 mm/min with a 25.4 mm (1 in)×101.6 mm (4 in) sample; and
    wherein said hydrated manufactured acellular dermal matrix is soaked in water for 5 minutes; and vi) a dry Youngs Modulus of at least 40 MPa for a dry manufactured acellular dermal matrix having no more than 20% moisture and a wet Youngs Modulus of at least 15 MPa for the hydrated manufactured acellular dermal matrix, wherein both the wet Youngs modulus and dry Youngs modulus are measured by said tensile test,
    wherein the manufactured acellular dermal matrix has less than 20% moisture as determined by a Thermogravimetric Analyzer; and
    wherein the manufactured acellular dermal matrix is not freeze dried or lyophilized and maintains a dry condition having no more than 20% water when maintained at standard temperature and pressure at less than 50% Rh, for a shelf life of at least 6 months.

2. The method of claim 1, wherein the enzymatic processing step preserves at least 70% of the native collagen structure.

3. The method of claim 1, wherein dehydrating the microbe-free acellular dermal matrix in a dehydration solution containing one or more of ethanol, methanol and acetone includes a series of washing in said dehydration solution with an increasing concentration of one or more of ethanol, methanol and acetone.

4. The method of claim 3, wherein the concentration of the dehydration solution ranges from 70% to 100%.

5. The method of claim 1, wherein the final processed acellular dermal matrix is characterized by a swelling ratio of no more than 50% in thickness after 30 minutes of hydration at room temperature, ensuring minimal expansion upon implantation.

6. The method of claim 1, wherein the sterilization process is performed using pera acetic acid and without gamma irradiation or ethylene oxide exposure, preserving native matrix bioactivity and mechanical integrity.

7. The method of claim 1, wherein the ionic solution comprises a sodium chloride solution.

8. The method of claim 1, further comprising meshing the acellular dermal matrix to produce a plurality of apertures through the acellular dermal matrix.

9. A method of making the manufactured acellular dermal matrix, the method comprising:

a) providing a mammalian skin tissue comprising:
  i) a collagen;
  ii) proteins including glycoproteins, and lipids;
  iii) genetic material including DNA;
  iv) cells with a cell membrane; and b) washing the mammalian skin tissue with an ionic solution at a concentration of 1M or more at a temperature of 40° C. or higher for at least 3 hours to disrupt the cell membranes and produce an epidermis free tissue;

c) washing the epidermis free tissue to a recombinant serine protease enzyme to destroy the cells while preserving the extracellular matrix to produce a processed dermal tissue;

d) removing residual lipids from the processed dermal tissue using an organic solvent or surfactant-based solution containing one or more of chloroform, methanol, hexane, or surfactants to produce a lipid extracted tissue;

e) washing the lipid extracted tissue with an acid solution containing 0.01% to 2% peracetic acid for at least 45 minutes to achieve microbial inactivation to produce a microbe-free acellular dermal matrix; and f) finishing the microbe-free acellular dermal matrix consisting of dehydrating the microbe-free acellular dermal matrix by washing the microbe-free acellular dermal matrix in a dehydration solution containing one or more of ethanol, methanol and acetone, and subsequently washing in xylene to selectively remove cellular debris and membrane lipids without disrupting collagen fiber organization to produce the manufactured acellular dermal matrix comprising:

i) at least 70% of the collagen;

ii) no more than 20 ng DNA/mg of the manufactured acellular dermal matrix;

iii) a solvent concentration of no more than 10 mg/g of manufactured acellular dermal matrix;

iv) a hydration rate, a time to double in weight when the manufactured acellular dermal matrix is soaked in water, of no more than 60 second;

v) an elongation at break when said manufactured acellular dermal matrix is a hydrated acellular dermal matrix of 50% or more as determined by a tensile test with a 25.4 mm (1 in) jaw gap and strain rate of 10 mm/min with a 25.4 mm (1 in)×101.6 mm (4 in) sample; and wherein said hydrated manufactured acellular dermal matrix is soaked in water for 5 minutes; and vi) a dry Youngs Modulus of at least 40 MPa for a dry manufactured acellular dermal matrix having no more than 20% moisture and a wet Youngs Modulus of at least 15 MPa for the hydrated manufactured acellular dermal matrix, wherein both the wet Youngs modulus and dry Youngs modulus are measured by said tensile test, and wherein the manufactured acellular dermal matrix has less than 20% moisture as determined by a Thermogravimetric Analyzer; and wherein the manufactured acellular dermal matrix is not freeze dried or lyophilized and maintains a dry condition having no more than 20% water when maintained at standard temperature and pressure at less than 50% Rh, for a shelf life of at least 6 months.

\* \* \* \* \*